United States Patent [19]

Crossley

[11] Patent Number: 4,678,794

[45] Date of Patent: Jul. 7, 1987

[54] N-PYRIDYL-SUBSTITUTED PYRIDINE-2-CARBOXAMIDE-1-OXIDES

[75] Inventor: Roger Crossley, Reading, England

[73] Assignee: John Wyeth & Brother Limited, Maidenhead, England

[21] Appl. No.: 795,065

[22] Filed: Nov. 5, 1985

[30] Foreign Application Priority Data

Nov. 6, 1984 [GB] United Kingdom .................. 8428007

[51] Int. Cl.$^4$ ..................... C07D 401/12; A61K 31/44
[52] U.S. Cl. ..................................... 514/332; 546/262
[58] Field of Search ......................... 546/262; 514/332

[56] References Cited

FOREIGN PATENT DOCUMENTS 154799  4/1982  German Democratic Rep. .

OTHER PUBLICATIONS

*Chemical Abstracts*, 92, 163232r (1980).
*Chemical Abstracts*, 89, 129359r (1978).
*Chemical Abstracts*, 92, 197359c (1980).

*Primary Examiner*—Jane T. Fan
*Attorney, Agent, or Firm*—George Tarnowski

[57] ABSTRACT

Compounds having the formula I

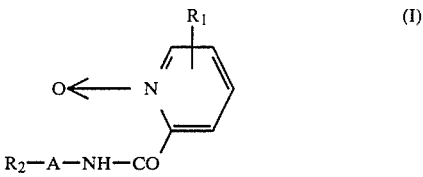

and their pharamaceutically acceptable acid addition salts, wherein $R_1$ is hydrogen or lower alkyl, A is a direct bond or lower alkylene and $R_2$ is pyridinyl or pyridinyl monosubstituted by lower alkyl, are useful as anti-ulcer agents and, in the case where A is a direct bond, as anti-secretory agents.

10 Claims, No Drawings

N-PYRIDYL-SUBSTITUTED PYRIDINE-2-CARBOXAMIDE-1-OXIDES

The invention relates to pyridine derivatives useful as pharmaceuticals, processes for their preparation and pharmaceutical compositions containing them.

The invention provides compounds having the formula I

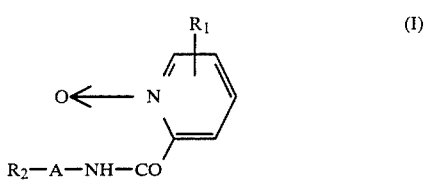

and their pharmaceutically acceptable acid addition salts for use as pharmaceuticals. In formula I $R_1$ is hydrogen or lower alkyl, A is a direct bond or lower alkylene and $R_2$ is pyridinyl, optionally monosubstituted by lower alkyl. The compounds are novel except where $R_1$ is methyl at the 6-position of the ring.

The term "lower" as used herein in respect of such groups as alkyl and alkylene indicates that the group contains 1-6, preferably 1-4 carbon atoms.

$R_1$ is hydrogen or lower alkyl, e.g. methyl or ethyl. $R_1$ is preferably hydrogen. A represents a direct bond or lower alkylene. The lower alkylene may be branched or a straight chain. Examples include methylene, dimethylene and trimethylene. A preferably represents a direct bond or methylene. $R_2$ is pyridyl, i.e. 2-, 3- or 4- pyridyl, preferably 2-pyridyl which may be unsubstituted or monosubstituted by lower alkyl, for example, methyl or ethyl.

Examples of acid addition salts are those formed from inorganic and organic acids, for instance, hydrochlorides, hydrobromides, hydroiodides, sulphates, nitrates, phosphates, sulphonates (e.g. the methane-sulphonate or p-toluene sulphonate), acetate, maleate, citrate, fumarate, tartrate, malonate and formate.

The compounds of the invention may be prepared by a process in which an amine having the formula $R_2$—A—$NH_2$ (II) (where $R_2$ and A are as defined above) or a reactive derivative thereof is coupled with an acid having the formula III

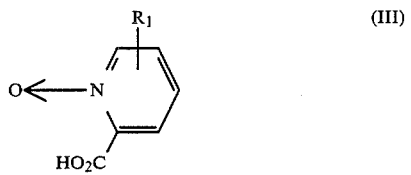

(where $R_1$ is as defined above) or a reactive derivative thereof. If desired the process may also include conversion of an acid addition salt of the compound having formula I into the compound of formula I by neutralisation with a base or conversion of a compound having formula I into a pharmaceutically acceptable salt thereof by addition of an acid.

The coupling reaction may be carried out by reacting the amine II with the acid III in the presence of a condensing agent, for instance, a carbodiimide. The use of 1,1'-carbonyldiimidazole as condensing agent is recommended. Alternatively, the acid III may be reacted with a compound in which the amino function of the amine II has been activated, for instance, by forming the phosphazo derivative. The coupling may be carried out by reacting the amine II with a reactive derivative of the acid III, for example, active esters, acyl halides, simple or mixed anhydrides and the acid azide. The acid halides, particularly the acid chloride, are especially suitable. The reaction product can be recovered from the reaction mixture by standard isolation procedures.

The amines II and acids III are generally known or, if new, can be prepared in known manner.

The compounds having formula I are indicated for use as pharmaceuticals. They are useful as anti-ulcer agents and are indicated for treatment of peptic ulcer diseases. Where A is a direct bond, the compounds are also anti-secretory agents and may be used to treat gastric hypersecretion. The compounds may be tested as anti-ulcer agents by assessing their effect upon gastric ulcers caused in rats by cold-restraint stress, in particular by a modification of the procedure of H.M. Manson and D.A. Brodie, J. Appl. Physiol., 15, 291–294 (1960). The end compounds of Examples 1 and 2 herein, when so tested, exhibit activity at 100mg/kg p.o. Compounds may be tested for anti-secretory activity in known manner, in particular by the procedure of H. Shay, D. Sun and M. Gruenstein, Gastroenterology 26:906-913 (1954). The end compound of Example 1, when so tested, exhibits activity at 30mg/kg id.

The invention also includes pharmaceutical compositions containing a compound having formula I or a pharmaceutically acceptable salt thereof in association or combination with a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The invention is illustrated by the following Examples:

EXAMPLE 1

N-(Pyridin-2-yl)pyridine-2-carboxamide-1-oxide 1,1'-Carbonyldiimidazole (4.254 g, 26.2 mol) was added to a solution of picolinic acid N-oxide (3.318g, 23.9 mol) in dry dimethylformamide (50 ml). After 4 hours, 2-aminopyridine (2.466 g, 26.2 mol) was added. After 1 hour, the solution was warmed to 100° for 80 minutes and cooled to room temperature. After 18 hours the solution was subjected to evaporation in vacuo to give an oil which slowly crystallised. The solid was recrystallised from EtOH to give the title compound (3.775 g) as needles, m.p. 140°–5°.

Analysis

Found: C, 61.8%; H, 4.05%; N, 20.0%.

$C_{11}H_9N_3O_2$ requires C, 61.4%; H, 4.2%; N, 19.5%.

EXAMPLE 2

N-(Pyridin-2-ylmethyl)pyridine-2-carboxamide-1-oxide 1,1'-Carbonyldiimidazole (4.461 g, 27.5 mol) was added to a solution of picolinic acid N-oxide (3.479 g, 25.0 mol) in dry DMF (50ml). After 4 hours, 2-aminomethylpyridine (2.84 ml, 27.5 mol) was added. After 2 hours, the solution was evaporated in vacuo to give a yellow oil. The oil was dissolved in water (50 ml) and the solution was extracted with methylene chloride (3×70 ml). The extracts were dried (MgSO4) and evaporated in vacuo to give an oil which was purified by chromatography [Al₂O₃;CH₂Cl₂–MeOH (50:1)]to give an oil which slowly crystallised as the title compound (3.299 g), m.p. 85°–94°.

Analysis

Found: C, 62.8%; H, 4.6%; N, 18.5% .;

C12H11N3O2 requires C, 62.9%; H, 4.8%; N, 18.3%.

I claim:

1. A pharmaceutical composition useful as an anti-ulcer agent comprising an effective amount of a compound having the formula I

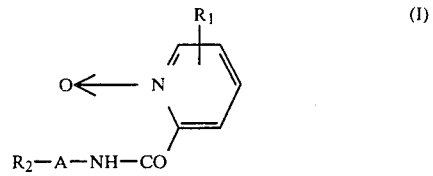

or a pharmaceutically acceptable acid addition salt thereof wherein $R_1$ is selected from hydrogen and lower alkyl, A is selected from a direct bond and lower alkylene and $R_2$ is selected from pyridinyl and pyridinyl monosubstituted by lower alkyl, in association or combination with a pharmaceutically acceptable carrier.

2. A pharmaceutical composition as claimed in claim 1, wherein the compound having formula I is N-(pyridin-2-yl)pyridine-2-carboxamide-1-oxide.

3. A pharmaceutical composition as claimed in claim 1, wherein the compound having formula I is N-(pyridin-2-ylmethyl)pyridine-2-carboxamide-&-oxide.

4. A pharmaceutical composition useful as an anti-secretory agent comprising an effective amount of a compound selected from those having the formula Ia

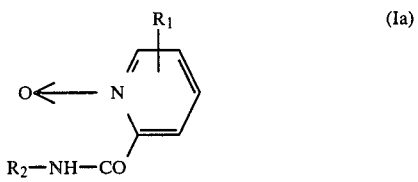

or a pharmaceutically acceptable acid addition salt thereof wherein $R_1$ is selected from hydrogen and lower alkyl and $R_2$ is selected from pyridyl and pyridyl monosubstituted by lower alkyl, in association or combination with a pharmaceutically acceptable carrier.

5. A pharmaceutical composition as claimed in claim 4, wherein the compound having formula Ia is N-(pyridin-2-yl)pyridine-2-carboxamide-1-oxide.

6. A method for the treatment of a subject in need of an anti-ulcer agent, which comprises administering to the subject an effective amount of a compound having the formula I

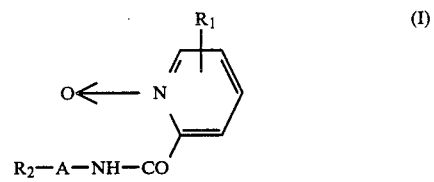

or a pharmaceutically acceptable salt thereof, wherein $R_1$ is selected from hydrogen and lower alkyl, A is selected from a direct bond and lower alkylene and $R_2$ is selected from pyridinyl and pyridinyl monosubstituted by lower alkyl.

7. A method for the treatment of a subject in need of an anti-secretory agent, which comprises administering to the subject an effective amount of a compound having the formula Ia

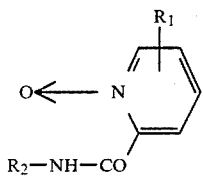

or a pharmaceutically acceptable salt thereof, wherein R₁ is selected from hydrogen and lower alkyl and R₂ is selected from pyridinyl and pyridinyl monosubstituted by lower alkyl.

8. A compound having the formula I

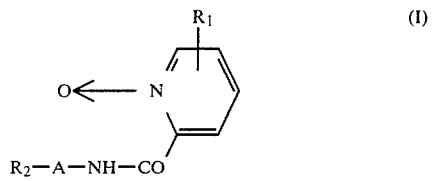

and their pharmaceutically acceptable salt thereof, wherein R₁ is selected from hydrogen and lower alkyl subject to the proviso that R₁ is other than methyl at the 6- position; A is selected from a direct bond and lower alkylene and R₂ is selected from pyridinyl and pyridinyl monosubstituted by lower alkyl.

9. A compound as claimed in claim 8, which is N-(pyridin-2-yl)pyridine-2-carboxamide-1-oxide or a pharmaceutically acceptable salt thereof.

10. A compound as claimed in claim 8, which is N-(pyridin-2-ylmethyl)pyridine-2-carboxamide-1-oxide or a pharmaceutically acceptable salt thereof.

* * * * *